United States Patent [19]

Jackson

[11] Patent Number: 5,352,699
[45] Date of Patent: Oct. 4, 1994

[54] USE OF RETINIOC ACID TO TREAT VAGINAL ATROPHY

[75] Inventor: Connie Jackson, Brookline, Mass.

[73] Assignee: University of Massachusetts Medical Center, Worcester, Mass.

[21] Appl. No.: 150,763

[22] Filed: Nov. 12, 1993

Related U.S. Application Data

[63] Continuation of Ser. No. 876,495, Apr. 30, 1992, abandoned.

[51] Int. Cl.$^5$ ............................................. A61K 31/20
[52] U.S. Cl. .................................... 514/559; 514/967
[58] Field of Search ................................ 514/559, 967

[56] References Cited

PUBLICATIONS

CA 108(5):36588k, Silva et al., 1987.
CA 98(9):70742r, Stephens–Jarnagin et al., 1983.

Primary Examiner—Marianne M. Cintins
Assistant Examiner—Kimberly R. Jordan
Attorney, Agent, or Firm—Fish & Richardson

[57] ABSTRACT

A method for the treatment of vaginal atrophy in a human patient in which retinoic acid is administered topically to the patient's vagina.

4 Claims, No Drawings

USE OF RETINIOC ACID TO TREAT VAGINAL ATROPHY

This is a continuation of application Ser. No. 07/876,495, filed Apr. 30, 1992, now abandoned.

BACKGROUND OF THE INVENTION

This invention relates to vaginal atrophy.

Vaginal atrophy is a condition occurring in some women, typically postmenopausal women, in which there is significant thinning of the mucosa of the vagina. The thin vaginal mucosa lacks maturation, i.e., it consists of numerous parabasal cells and little or no superficial and intermediate cells, which results in decreased glycogen deposits and a higher pH.

Symptoms resulting from the abnormally thin vaginal mucosa include vaginal dryness, discomfort, itching, dyspareunia, infection, inflammation, ulcers, discharge, and bleeding Vaginal atrophy is caused chiefly by an estrogen deficiency; the mucosa of the vagina is an estrogen sensitive tissue and a well-known target organ for estrogen.

The administration of exogenous estrogen can dramatically reverse the atrophic process by causing the vaginal epithelium to undergo proliferation and maturation, causing an increase in superficial and intermediate cells, and thereby causing an increase in vaginal mucosal thickness. The administration of exogenous estrogen also influences glycogen deposits and vaginal acidity. Many postmenopausal women are however unable to use estrogens due to medical contraindications such as a history of breast, endometrial or ovarian cancer and various hematological disorders. In addition, some postmenopausal women who would benefit from estrogen replacement do not receive replacement due to fears of estrogens in general or undesirable side effects. The treatment of vaginal atrophy in patients who do not use exogenous estrogen is a significant therapeutic problem; most of these women are forced to endure their symptoms due to the lack of effective treatment alternatives.

SUMMARY OF THE INVENTION

The invention features a method of treating vaginal atrophy in a human patient by topically administering retinoic acid to the patient's vagina.

The treatment is effective and safe for those patients who cannot or will not use exogenous estrogen.

Other features and advantages of the invention will be apparent from the following description of the preferred embodiments thereof, and from the claims.

DESCRIPTION OF THE PREFERRED EMBODIMENT(S)

In one preferred embodiment, retinoic acid in a cream base is applied topically to the vagina of a patient with vaginal atrophy. The concentration of the retinoic acid is sufficient to provide therapeutic results with respect to the treatment of vaginal atrophy while at the same time low enough to minimize side effects of erythema of the vulva and inner thighs. Preferably, the retinoic acid is provided in a carrier suitable for topical use, in a concentration of 0.025% to 0.05% by weight, to provide a dosage of 0.125 to 0.50 mg per day. In addition to creams and ointments, the carrier can be in a form of a suppository, which provides advantages in terms of application, and also eliminates the need to measure the amount of medicament applied.

CLINICAL STUDIES

Fourteen patients were selected for a study, which was carried out by C. Jackson from January, 1991 to July 1991 at the University of Massachusetts Medical Center and The Cental Medical Center of Massachusetts in Worcester. All of the patients were post menopausal women who suffered from the symptoms of vaginal atrophy.

The study was a double-blind randomized study using placebo, 0.025%, and 0.050%, by weight trans-retinoic acid (Retin-A) cream which was manufactured by Ortho Pharmaceutical Corporation. Drug effects were monitored using patient symptomatology, clinical pelvic examination along with vaginal cytology and histology. Papanicolaon ("Pap") smears were obtained from the upper ⅓ lateral vaginal wall in the routine manner for maturation index. This latter test was analyzed to determine the ratio of superficial, intermediate, and parabasal cells. Biopsy specimens were obtained from the upper one-third of the vagina using a Kevorkian forceps after application of topical 4% lidocaine. Histologic specimens were evaluated for epithelial thickness and the presence or absence of glycogen, a measure of vaginal epithelial maturation.

The fourteen patients who took part in the study were screened by history and physical examination. Symptomatology related to vaginal atrophy as well as any systemic complaints were elicited and recorded. The physical exam included a description of the vaginal mucosa. The presence or absence of erythema, vascularity, ulceration, bleeding, friability, and vaginal rugae were noted.

After informed consent, the patients were randomized to a specific dose and given a coded tube. An initial pap smear and vaginal biopsy were obtained at the first visit. Each woman was instructed to charge the vaginal applicator and administer the dose vaginally daily for seven consecutive days, preferably at night. Some of the patients used a half a gram and others used a gram according to the randomized dosages. Each patient returned after seven days to report any problems or side effects associated with use of the drug. A pelvic examination was performed as well as a vaginal pap smear and biopsy, and a clinical description of the vaginal mucosa was taken. The process was repeated monthly for three consecutive months. A biopsy and pap smear were obtained at the beginning of the second cycle. Thereafter, only pap smears were obtained for evaluation. Each woman was questioned regarding her ability to adhere to the daily dosage regimen. Used tubes were collected to determine if the proper amount of medication was used. Dr. Jackson performed three biopsies and six pap smears on each patient in the study.

Based upon the initial biopsies taken, two of the twelve patients who suffered from symptoms associated with vaginal atrophy did not, in fact, have true vaginal atrophy. These two patients were taking oral estrogens. It is a well-known clinical fact that women who take oral estrogen may still experience the symptoms of vaginal atrophy.

All fourteen patients who enrolled completed the study. All patients that received Retin-A reported relief of atrophy related symptoms to various degrees. Three of the five patients who received placebo reported some subjective improvement in their atrophy related symptoms. Five of the nine patients given retinoic acid showed changes in their cytological and/or histological specimens. (One patient showed changes in both; two patients showed changes in only cytology; and two patients showed changes only in histology.) 33% of these patients showed a definite improvement in vaginal epithelial thickness. Cytologies tended to suggest improved cellular proliferation and maturation as well. Many patients experienced undesirable vulva side effects from the application of intravaginal Retin-A, which included mild erythema of the vulva and inner thighs and associated itching and burning in some. Zinc oxide cream and mild steroid creams were applied to the vulva and inner thighs when these side effects were encountered. The topical application of zinc oxide cream prior to the application of Retin A helped reduce side effects significantly.

Other embodiments are within the scope of the following claims.

What is claimed is:

1. A method of treating vaginal atrophy in a human patient comprising topically administering retinoic acid to said patient's vagina, said retinoic acid being administered in a dosage sufficient to ameliorate the symptoms of vaginal atrophy.

2. The method of claim 1 in which said retinoic acid is trans-retinoic acid.

3. The method of claim 1 in which said retinoic acid is combined with a pharmaceutically acceptable carrier substance.

4. The method of claim 1, further comprising the step, prior to administration of retinoic acid, of topically administering zinc oxide cream to the vulva of said patient.

* * * * *